(12) United States Patent
Goldfine et al.

(10) Patent No.: US 8,928,316 B2
(45) Date of Patent: Jan. 6, 2015

(54) METHOD AND APPARATUS FOR NON-DESTRUCTIVE EVALUATION OF MATERIALS

(75) Inventors: Neil J. Goldfine, Newton, MA (US); Andrew P. Washabaugh, Chula Vista, CA (US); Robert Lyons, Pelham, MA (US); Zachary Thomas, Cambridge, MA (US); David A. Jablonski, Whitman, MA (US); Christopher Martin, Concord, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 411 days.

(21) Appl. No.: 13/297,933

(22) Filed: Nov. 16, 2011

(65) Prior Publication Data

US 2012/0126803 A1    May 24, 2012

Related U.S. Application Data

(60) Provisional application No. 61/414,008, filed on Nov. 16, 2010, provisional application No. 61/524,520, filed on Aug. 17, 2011.

(51) Int. Cl.
*G01R 33/12* (2006.01)
*G01N 27/82* (2006.01)
*G01R 33/10* (2006.01)
*G01R 33/00* (2006.01)

(52) U.S. Cl.
CPC ............ *G01R 33/10* (2013.01); *G01R 33/0064* (2013.01); *G01R 33/0094* (2013.01)
USPC ............ 324/242; 324/238; 324/239; 324/243

(58) Field of Classification Search
USPC ......... 324/216, 228, 237–240, 456, 500, 512, 324/519, 658, 661, 686, 718, 754.28; 702/35, 38, 47, 52, 57–59, 127, 182, 702/183, 185; 73/760, 763, 774, 780, 73/862.626, 335.04
See application file for complete search history.

(56) References Cited

U.S. PATENT DOCUMENTS

| 4,348,635 | A | * | 9/1982 | Wright et al. | ................. 324/559 |
| 4,814,690 | A | | 3/1989 | Melcher et al. | |
| 5,015,951 | A | * | 5/1991 | Melcher | ........................ 324/232 |

(Continued)

OTHER PUBLICATIONS

ASTM WK8211 "Standard Guide for Nondestructive Testing of Polymer Matrix Composites Used in Aerospace Applications," Designation: E2533-09, (Jul. 2009).

(Continued)

*Primary Examiner* — Hoai-An D Nguyen
(74) *Attorney, Agent, or Firm* — Hamilton, Brook, Smith & Reynolds, P.C.

(57) ABSTRACT

Methods and apparatus for characterizing composite materials for manufacturing quality assurance (QA), periodic inspection during the useful life, or for forensic analysis/material testing. System are provided that relate eddy-current sensor responses to the fiber layup of a composite structure, the presence of impact damage on a composite structure with or without a metal liner, volumetric stress within the composite, fiber tow density, and other NDE inspection requirements. Also provided are systems that determine electromagnetic material properties and material dimensions of composite materials from capacitive sensor inspection measurements. These properties are related to the presence of buried defects in non-conductive composite materials, moisture ingress, aging of the material due to service or environmental/thermal exposure, or changes in manufacturing quality.

8 Claims, 12 Drawing Sheets

(56) References Cited

U.S. PATENT DOCUMENTS

| | | | |
|---|---|---|---|
| 5,345,514 A * | 9/1994 | Mahdavieh et al. | 382/152 |
| 5,453,689 A | 9/1995 | Goldfine et al. | |
| 5,747,999 A * | 5/1998 | Yamaoka | 324/501 |
| 5,895,439 A * | 4/1999 | Fisher et al. | 702/36 |
| 6,188,218 B1 * | 2/2001 | Goldfine et al. | 324/243 |
| 6,380,747 B1 | 4/2002 | Goldfine et al. | |
| 6,784,662 B2 * | 8/2004 | Schlicker et al. | 324/242 |
| 6,992,482 B2 | 1/2006 | Shay et al. | |
| 7,161,350 B2 * | 1/2007 | Goldfine et al. | 324/238 |
| 7,839,282 B1 * | 11/2010 | Mathur et al. | 340/562 |
| 8,264,243 B2 * | 9/2012 | Tarui et al. | 324/663 |
| 2003/0071615 A1 * | 4/2003 | Schlicker et al. | 324/242 |
| 2003/0164700 A1 * | 9/2003 | Goldfine et al. | 324/235 |
| 2004/0004475 A1 * | 1/2004 | Goldfine et al. | 324/242 |
| 2004/0056654 A1 * | 3/2004 | Goldfine et al. | 324/239 |
| 2004/0066188 A1 * | 4/2004 | Goldfine et al. | 324/228 |
| 2004/0225474 A1 * | 11/2004 | Goldfine et al. | 702/183 |
| 2004/0232911 A1 * | 11/2004 | Schlicker et al. | 324/242 |
| 2007/0120561 A1 * | 5/2007 | Goldfine et al. | 324/238 |
| 2010/0045277 A1 * | 2/2010 | Goldfine et al. | 324/209 |
| 2012/0123699 A1 * | 5/2012 | Kawata et al. | 702/35 |

OTHER PUBLICATIONS

Goldfine, "Magnetometers for Improved Materials Characterization in Aerospace Applications," Materials Evaluation, pp. 396-405, (Mar. 1993).

Goldfine, "Uncalibrated, Absolute Property Estimation and Measurement Optimization for Conducting and Magnetic Media Using Imposed w-k Magnetometry," Doctoral Thesis, Massachusetts Institute of Technology, Cambridge, MA, pp. 1-139, (Sep. 1990).

Goldfine, et al., "Eddy Current Sensor Networks for Aircraft Fatigue Monitoring," ASNT Materials Evaluation, Aerospace Health Monitoring, 61(7):1-13, (Jul. 2003).

Goldfine, et al., "Rapid Nonlinear 'System' Identification for NDT, Using Sensor Response Databases," Mat. Eval., 66(7):1-12, (Jul. 2008).

Hashin, "Analysis of Properties of Fiber Composites with Anisotropic Constituents," J. App. Mech., 46(3):543-550, (Sep. 1979).

Melcher, "Continuum Electromechanics," The MIT Press, Cambridge, MA (1981).

Park, J.B., et al., "Electromechanical Modeling of Unidirectional CFRP Composites under Tensile Loading Condition," Composites: Part A, 33:267-275, (2002).

Russell, John D., "Composites Affordability Initiative: Transitioning Advanced Aerospace Technologies through Cost and Risk Reduction," The AMMTIAC Quarterly, 1(3):3-6, (2006).

Wang, X., et al., "Electromechanical Behavior of Carbon Fiber," Carbon, 35(5): 452-453, (1997).

Wang, X., et al., "Electromechanical Study of Carbon Fiber Composites," J. Mater. Res., 13 (11):3081-3092, (Nov. 1998).

* cited by examiner

METHOD AND APPARATUS FOR NON-DESTRUCTIVE EVALUATION OF MATERIALS

RELATED APPLICATIONS

This application claims the benefit of U.S. Provisional Application No. 61/414,008, filed on Nov. 16, 2010 and U.S. Provisional Application No. 61/524,520, filed on Aug. 17, 2011.

The entire teachings of the above applications are incorporated herein by reference.

GOVERNMENT SUPPORT

This invention was made with government support under contract number NNX10CB25C awarded by NASA and contract number NNX11CG49P awarded by NASA. The government has certain rights in the invention.

BACKGROUND

Composite materials are replacing traditional materials in aerospace and other industries because of their high strength to weight ratio, thermal characteristics, and other properties that can often be engineered for superior performance. For example, Organic and Ceramic Matrix Composites (CMCs) are being developed for high-temperature aerospace applications because of their light weight, high strength, superior wear resistance and dimensional stability at high temperatures. Components using these materials are being investigated for several engines.

Composite materials are not without their flaws and testing and validation is needed for quality control at production and for life management once deployed. Continuing the above example, CMCs that are most useful in aerospace structural applications have continuous fiber reinforcements embedded in a ceramic matrix. As such, these CMCs have mostly fiber-dominated mechanical properties and rely on the matrix materials for load transfer, increased strain and toughness, and, to some extent, environmental protection. However, at the elevated temperature environments typically found in advanced propulsion systems, these materials can react with the oxygen, moisture, and salt in the air to undergo chemical changes that can affect the structural performance and remaining life of components made from these materials, while showing no visible structural changes.

Nondestructive evaluation (NDE) techniques are needed that can provide relevant information about the material condition of the composite and constituents. These techniques also need to provide information about the influence of any degradation or changes in these constituents on the ultimate performance of a composite materials. This information can be used to both improve operational performance and reduce costs by improving repair/replace decisions. Also, there is a need for enhanced NDE and stress monitoring for carbon fiber composites including the need to rapidly image manufacturing quality for wide areas curved surfaces, to detect and characterize impact and fatigue/overload damage, to monitor stress and detect cracks in metal structural elements behind composite layers.

SUMMARY

Methods and apparatus are disclosed for characterizing composite materials for manufacturing quality assurance (QA), periodic inspection during the useful life, or for forensic analysis/material testing. System are provided that relate eddy-current sensor responses to the fiber layup of a composite structure, the presence of impact damage on a composite structure with or without a metal liner, volumetric stress within the composite, fiber tow density, and other NDE inspection requirements. Also provided are systems that determine electromagnetic material properties and material dimensions of composite materials from capacitive sensor inspection measurements. These properties are related to the presence of buried defects in non-conductive composite materials, moisture ingress, aging of the material due to service or environmental/thermal exposure, or changes in manufacturing quality.

In one aspect the invention relates to a system for detecting impact damage to an object. The system comprises: an eddy-current sensor array having a plurality of array elements; a fixture for scanning the eddy-current sensor array over a surface of the object; an instrument for measuring impedancesfrom each of the array elements of the array during scanning; a processor; and a plurality of modules comprising code executable by the processor, the plurality of modules comprising an imaging module to generate a current material property image from the impedances measured by the instrument; and a detection module to determine from the current material property image locations of impact damage.

The system of may further comprise a computer-readable storage device for recording a prior material property image obtained from impedance measurements of an earlier scan of the object, wherein the detection module subtracts the current material property image from the prior material property image to identify locations with material property changes in excess of a threshold.

The system of may be such that the material property is a local distance of the eddy-current sensor array to a surface of the object.

Another aspect relates to a method of inspecting a composite overwrap pressure vessel (COPV). The method comprises scanning a linear drive eddy-current sensor array proximal to the COPV parallel to a surface of the COPV; measuring, during the scanning, first impedances at each of a plurality of sense elements of the array, while exciting the sensor at a first frequency; measuring, during the scanning, second impedances at each of the plurality of sense elements of the array, while exciting the sensor at a second frequency, lower than the first frequency; processing the first impedances to obtain a first property image characterizing the composite overwrap of the COPV; processing the second impedances to obtain a second property image characterizing a metal liner of the COPV; analyzing the first and second property images to determine damage in the composite overwrap and the metal liner of the COPV, respectively.

The analysis may comprise registering a previously captured image of the respective property and determining a difference between the two; comparing the differences to a respective threshold to identify locations of damage; and determining an amount of damage at the locations of damage based on an amount of change in the property in (e.g., excess of the threshold).

Another aspect relates to a method of inspecting a composite overwrap pressure vessel (COPV). The method comprises scanning an eddy-current sensor proximal to the COPV parallel to a surface of the COPV; during the scanning, measuring first impedances while exciting a linear drive of the sensor; during the scanning, measuring second impedances while exciting a non-linear shaped drive of the sensor; processing the first impedances to obtain a first property image characterizing the composite overwrap of the COPV; processing the second impedances to obtain a second property image characterizing a metal liner of the COPV; and analyzing the first and second property images to determine damage in the composite overwrap and the metal liner of the COPV, respectively.

Another aspect relates to a system for determining a layup of a composite structure. The system has an eddy-current sensor; a fixture for maintaining the eddy-current sensor proximal to a location on the composite structure and rotating the sensor relative to the location; an instrument for measuring impedances from the eddy-current sensor during the rotation; a processor; and at least one module comprising code executable by the processor, the at least one modules comprising a relationship module for relating impedance measurements at one or more angles of the eddy-current sensor to respective fiber orientations within the composite structure. The system may be used, for example, to inspect a composite overwrapped pressure vessel (COPV).

The system may be such that the at least one modules further comprise a validation module that validates that the fiber orientations at the location on the composite structure are within a specification. Further, the system may be such that the fixture is further configured to position the eddy-current sensor at a plurality of other locations on the composite structure and the validation module validates the fiber orientations at each of the plurality of other locations.

Another aspect relates to a system for identifying defects in a low-conductivity fiber composite. The system has a capacitive sensor; a fixture for scanning the capacitive sensor array over a surface of the low-conductivity fiber composite; an instrument for measuring impedances from the capacitive sensor during the scanning; a processor; and a plurality of modules comprising code executable by the processor, the plurality of modules comprising an imaging module to generate a current material property image from the impedances measured by the instrument; and a detection module to determine from the current material property image locations of defects in a low-conductivity fiber composite.

The system may be such that the capacitive sensor is a capacitive sensor array.

Another aspect relates to a system for determining a density of fiber tows in a composite. The system comprises a eddy-current sensor having a linear drive construct; a fixture for maintaining the linear drive construct parallel to a direction of fibers and for scanning the sensor across the fiber tows; an instrument for measuring impedances from the eddy-current sensor during the scanning; a processor; and at least one module comprising code executable by the processor, the at least one modules comprising a transformation module for transforming the impedances measured during scanning into a spatial parameter equivalent to the density of the fiber tows.

The system may be such that the spatial parameter is a spatial frequency of the fiber tows or a spatial periodicity of the fiber tows.

The system may be such that the at least one modules further comprise a validation module configured to compare the spatial parameter to an acceptable range of spatial parameters and to make an accept/reject decision based on whether the spatial parameter is within the acceptable range.

The system may be such that a fast Fourier transform (FFT) is used in converting impedance measurements into the spatial parameter.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized and appreciated the need for non-destructive evaluation (NDE) techniques for composite materials. Methods and apparatus are disclosed for NDE inspection of "conductive" and "non-conductive" composites. As used herein, conductive composites have a fiber/matrix conductivity of about $10^2$ S/m or greater, while non-conductive composites have a conductivity less than about $10^{-3}$ S/m. NDE of conductive composites may be performed by eddy-current sensor constructs with linear drive conductor segments, and NDE of non-conductive composites may be performed by capacitive sensor technologies.

Conductive composites include carbon fiber composites, reinforced carbon-carbon composites (RCC), metal matrix composites, as well as other composites with conducting fibers or a conducting matrix with conductivities above $10^2$ S/m. The inventors have recognized and appreciated that the electromagnetic material properties and material dimensions estimated from eddy-current inspection measurements may be related to the manufacturing quality, damage, stress, thermal or environmental usage condition of the composite materials inspected. Methods and apparatus are disclosed that relate eddy-current sensor responses to the fiber layup of a composite structure, the presence of impact damage on a composite structure with a metal liner, volumetric stress within the composite, fiber tow density, and other NDE inspection requirements needed for manufacturing quality assurance (QA) and periodic inspection during the useful life, or for forensic analysis/material testing.

Non-conductive composites include glass fiber composites, ceramic matrix composites (CMCs), organic matrix composites, heterogeneous construction materials (e.g., asphalt, concrete, cement) pharmaceuticals/pills with particle suspensions, and other heterogeneous materials with low effective bulk conductivities. The inventors have recognized and appreciated that the electromagnetic material properties and material dimensions estimated from capacitive sensor inspection measurements may be related to the presence of buried defects in non-conductive composite materials, moisture ingress, aging of the material due to service or environmental/thermal exposure, or changes in manufacturing quality.

Figure 1:
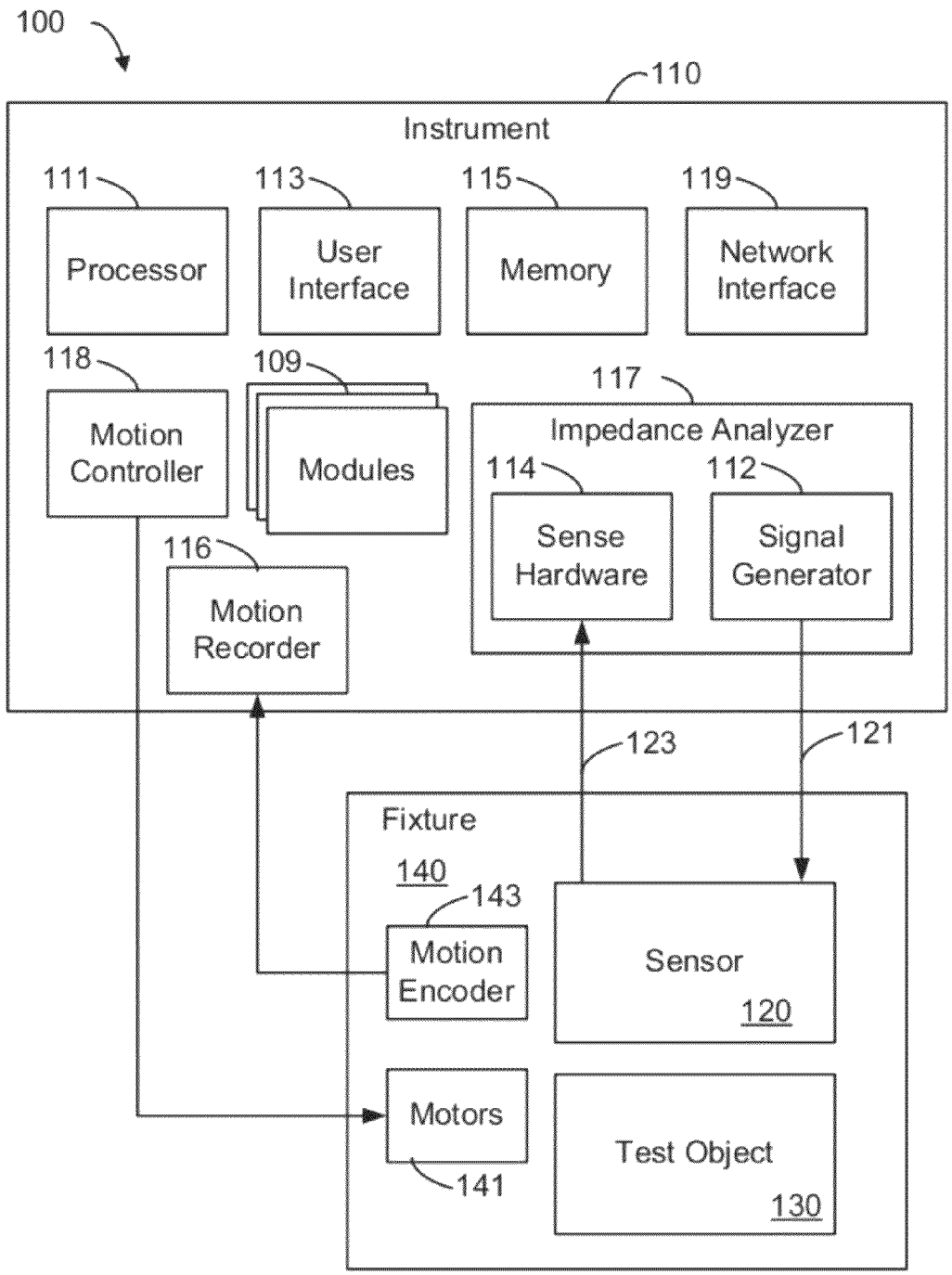
FIG. 1 is a block diagram of a system for measuring or monitoring properties of composite test objects according to some embodiments.

FIG. 1 is a block diagram of a system 100 for inspecting a test object 130. System 100 includes an instrument 110 and a sensor 120. Instrument 110 is configured to provide excitation signals 121 to sensor 120 and measure the resulting response signals 123 of sensor 120. Measured response signals 123 may be processed to estimate properties of interest, such as electrical properties (e.g., conductivity, permeability, and permittivity), geometric properties (e.g., thickness, sensor lift-off), material condition, or any other suitable property or combination thereof.

Instrument 110 may include a processor 111, a user interface 113, memory 115, an impedance analyzer 117, and a network interface 119. Though, in some embodiments of instrument 110 may include other combinations of components. While instrument 110 is drawn as a single block, it should be appreciated that instrument 110 may be physically realized as a single "box"; multiple, operably-connected "boxes", or in any other suitable way. For example, in some embodiments it may be desired to provide certain components of instrument 110 as proximal to sensor 120 as practical, while other components of instrument 110 may be located at greater distance from sensor 120.

Processor 111 may be configured to control instrument 110 and may be operatively connected to memory 115. Processor 111 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any suitable processing device. In some embodiments, processor 111 comprises one or more processors, for example, processor 111 may have multiple cores and/or be comprised of multiple microchips.

Memory 115 may be integrated into processor 111 and/or may include "off-chip" memory that may be accessible to processor 111, for example, via a memory bus (not shown). Memory 115 may store software modules that when executed by processor 111 perform desired functions. Memory 115 may be any suitable type of non-transient computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 110 may have one or more functional modules 109. Modules 109 may operate to perform specific functions such as processing and analyzing data. Modules 109 may be implemented in hardware, software, or any suitable combination thereof. Memory 115 of instrument 110 may store computer-executable software modules that contain computer-executable instructions. For example, one or more of modules 109 may be stored as computer-executable code in memory 115. These modules may be read for execution by processor 111. Though, this is just an illustrative embodiment and other storage locations and execution means are possible.

Instrument 110 provides excitation signals for sensor 120 and measures the response signal from sensor 120 using impedance analyzer 117. Impedance analyzer 117 may contain a signal generator 112 for providing the excitation signal to sensor 120. Signal generator 112 may provide a suitable voltage and/or current waveform for driving sensor 120. For example, signal generator 112 may provide a sinusoidal signal at one or more selected frequencies, a pulse, a ramp, or any other suitable waveform.

Sense hardware 114 may comprise multiple sensing channels for processing multiple sensing element responses in parallel. Though, other configurations may be used. For example, sense hardware 114 may comprise multiplexing hardware to facilitate serial processing of the response of multiple sensing elements. Sense hardware 114 may measure sensor transimpedance for one or more excitation signals at on one or more sense elements of sensor 120. Instrument 110 may process the transimpedance data to estimate one or more properties of test object 130. It should be appreciated that while transimpedance (sometimes referred to simply as impedance), may be referred to as the sensor response, the way the sensor response is represented is not critical and any suitable representation may be used.

Sensor 120 may be an eddy-current sensor, a dielectrometry sensor, an ultrasonic sensor, or utilize any other suitable sensing technology or combination of sensing technologies. In some embodiments, sensor 120 is a linear drive eddy-current sensor such as an MWM® or MWM®-Array available from JENTEK Sensors, Inc., Waltham, Mass. In another embodiment, sensor 120 is a interdigitated dielectrometry sensor or a segmented field dielectrometry sensor such as the IDED® sensors also available from JENTEK Sensors, Inc. Sensor 120 may have a single or multiple sensing and drive elements. Sensor 120 may be scanned across, mounted on, or embedded into test object 130.

In some embodiments, the computer-executable software modules may include a sensor data processing module, that when executed, estimates properties of the component under test. The sensor data processing module may utilize property grids stored in memory 115. The property grids are multi-dimensional pre-computed databases that relate one or more frequency transimpedance measurements to properties to be estimated. The sensor data processing module may take the property grids and sensor data and, using grid methods, estimate material properties.

User interface 113 may include devices for interacting with a user. These devices may include, by way of example and not limitation, keypad, pointing device, camera, display, audio input and audio output.

Network interface 119 may be any suitable combination of hardware and software configured to communicate over a network. For example, network interface 119 may be implemented as a network interface driver and a network interface card (NIC). The network interface driver may be configured to receive instructions from other components of instrument 110 to perform operations with the NIC. The NIC provides a wired and/or wireless connection to the network. The NIC is configured to generate and receive signals for communication over network. In some embodiments, instrument 110 is distributed among a plurality of networked computing devices. Each computing device may have a network interface for communicating with other the other computing devices forming instrument 110.

A fixture 140 may be used to position sensor 140 with respect to test object 130 and ensure suitable conformance of sensor 120 with test object 130. Fixture 140 may be a stationary fixture, manually controlled, motorized fixture, or a suitable combination thereof. For scanning applications where fixture 140 moves sensor 120 relative to test object 130, it is not critical whether sensor 120 or test object 130 is moved, or if both are moved to achieve the desired scan.

Fixture 140 may have one or more motors 141 that are controlled by motion controller 118. Motion controller 118 may control fixture 140 to move sensor 120 relative to test object 130 during an inspection procedure. Though, in some embodiments, relative motion between sensor 120 and test object 130 is controlled by the operator directly (e.g., by hand).

Regardless of whether motion is controlled by motion controller 118 or directly by the operator position encoders 143 of fixture 140 and motion recorder 116 may be used to record the relative positions of sensor 120 and test object 130.

Meandering winding eddy-current sensors and linear drive eddy-current sensor arrays may be constructed on thin, flexible substrates using relatively low cost microfabrication techniques, producing essentially identical sensors with essentially identical performance. These sensors may be conformed to the test object to provide high quality eddy current data over the coverage surface. No local electronics is required, dramatically enhancing survivability in harsh (hot, cold, vibrating, etc.) environments. A sensor can be scaled up or down, scaled in length or width, or both, and shaped in any suitable manner to fit a particular test object. Similarly, sensing elements can be made larger to increase coverage or smaller to increase spatial resolution, and strategically positioned to assure detection of events at key locations. Even very large footprint sensors can be extremely lightweight.

Figure 2A:
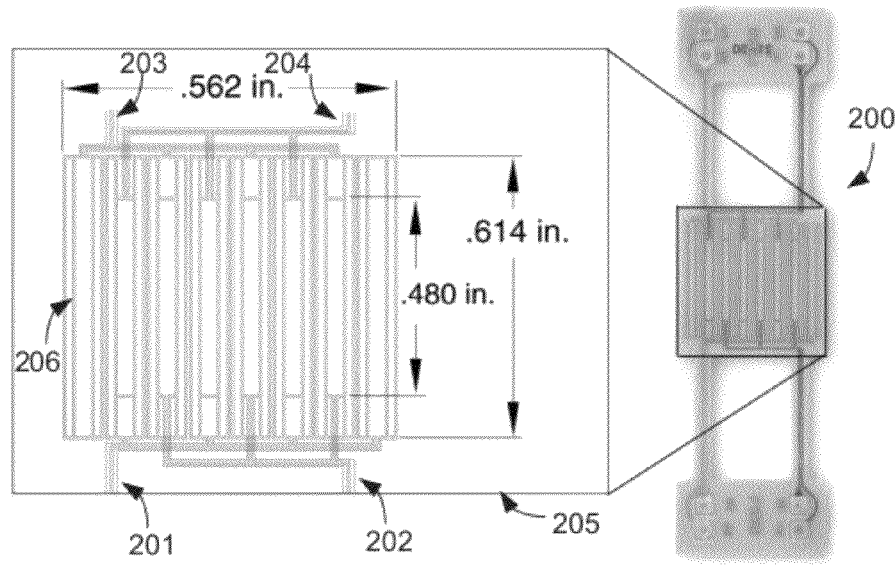
FIG. 2A is a meandering winding eddy-current sensor according to some embodiments.

FIG. 2A shows a meandering winding eddy-current sensor 200. Specifically, sensor 200 is an FS33 available under the trade name MMW® from JENTEK Sensors, Inc. The expanded area of sensor 200 is the active sensing area 205. This area includes a drive winding, sense winding, and additional guard elements 206. Leads 201 and 203 connect to the drive winding which receives the drive current (e.g., excitation signals 121) from the instrumentation. Leads 202 and 204 are connected to the sensing winding. The windings of the sensors resemble a square wave shape and are designed to produce a spatially periodic field. This field shape permits accurate modeling of the interaction with the material under test, thus significantly reducing calibration requirements. For example, in some situations an "air calibration" can be used, permitting measurement of a test object's absolute electrical conductivity without calibration standards. Furthermore, in-place recalibration and calibration verification are possible with these absolute-property sensors.

Figures 2B, 2C:
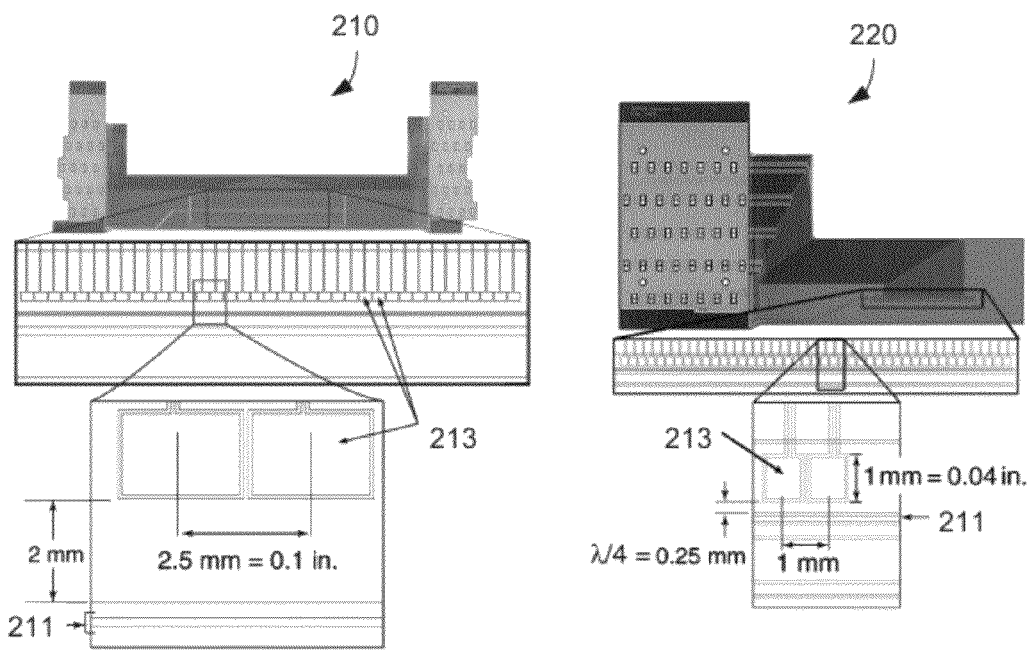
FIGS. 2B and 2C are linear drive eddy-current sensor arrays according to some embodiments.

FIGS. 2B and 2C show linear drive eddy-current sensor arrays 210 and 220, respectively. Array 210 is an FA24 and Array 220 is an FA28 sensor available under the trade name MMW-Array from JENTEK Sensors, Inc. These linear drive arrays have a linear drive construct 211 and a plurality of sensing elements 213.

Further description of meandering winding eddy-current sensor and linear drive eddy-current sensors may be found in U.S. Patent Publication No. 2010/0045277 titled "Magnetic field characterization of stresses and properties in materials" which is hereby incorporated by reference in its entirety.

The sensor responses are converted into material or geometric properties using measurement grids. These grids are used to convert two known values, such as the magnitude and phase (or real and imaginary parts) of the transimpedance, into the unknown properties of interest, such as electrical conductivity and lift-off. The grids are two-dimensional databases or pre-computed responses, which can be displayed graphically to support procedure development. Higher order databases are used for the determination of more than two unknown properties of interest.

Figure 3:
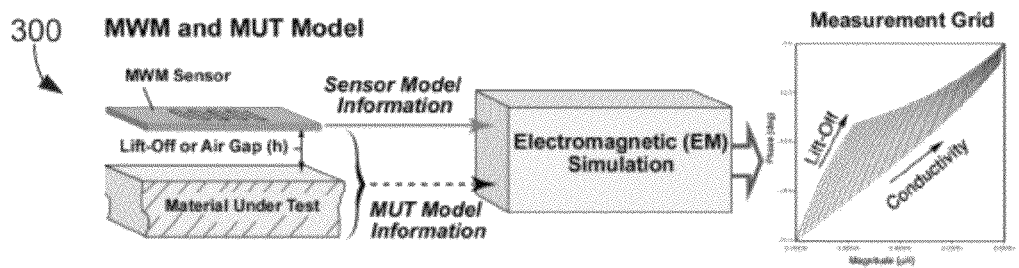
FIG. 3 is a flow diagram for generating measurement grids, lattices, and hyperlattices according to some embodiments.

The grids are generated using an analytical forward model and properties of the material under test (MUT) as illustrated schematically as process 300 in FIG. 3. In process 300 a model of the sensor (e.g., including relevant dimensions and identification of drive and sensing elements) in combination with a model of the material under test (MUT) are input to an electromagnetic simulator (e.g., analytical, semi-analytical, finite element) to compute the sensor response (e.g., impedance, admittance) at an excitation frequency. The computed sensor response (e.g., impedance) represents a point in the sensor response space (e.g., impedance plane). One or more input parameters to the simulation are changed and the simulation is repeated for the new input generating second and subsequent points in the parameter space. A grid is generated by selecting two input parameters to vary. Each input parameter is varied over selected values until every combination of input parameters has been simulated. In the example of a conductivity/lift-off grid, if lift-off and the conductivity each take 20 unique values a total of 400 simulations are performed to generate a grid. Each point in the sensor response space of the grid represents the sensor response for the specific parameters for the simulation. When a measurement is taken using a sensor and a MUT for which all parameters besides those varied when generating the grid are known to be in agreement with the constant values assumed in generating the grid, the measured sensor response can be plotted in the sensor response space. Assuming the grid is well behave and the measured sensor response is near the grid, the nearby grid points which are associated with specific values of the unknown parameters may be used to estimate what input parameters would have produced the sensor response that was actually measured. Further description of the grid methods is provided in U.S. Pat. No. 6,992,482 titled "Magnetic field sensor having a switchable drive current spatial distribution" which is hereby incorporated by reference in its entirety.

Another aspect relates to determination of fiber orientation in a composite material.

Fiber based composites consist of a fiber material and a matrix material. The fibers in a composite are often formed into plies or laminae ("sheets") with all the fibers in the ply in the same orientation. They may be weaved together into bundles or tows and the tows may be formed in a weave and these plies may be stacked up at various orientations intermixed with the matrix material to produce the composite structure.

When an eddy-current sensor with a linear drive construct, such as meandering winding eddy-current sensor 200 and linear drive eddy-current sensor array 220 (shown in FIGS. 2A and 2B, respectively), is placed such that the linear drive construct substantially aligns with the fiber of a conductive fiber composite material, a current is induced in the fiber. The sensor response of a linear drive eddy current sensor varies significantly depending on the orientation of the linear drive and the fibers. The plies forming the stack-up of some composites often have a predominant fiber orientation. This orientation may dominate the response of an eddy-current sensor. This orientation may be used to define the 0° angle. Though, any suitable reference orientation may be used. In a composite having multiple plies of various orientations the sensor may be aligned with a subset of the plies such that the response of the sensor is dominated by the condition of the plies with which the drive is aligned.

Figure 4A:
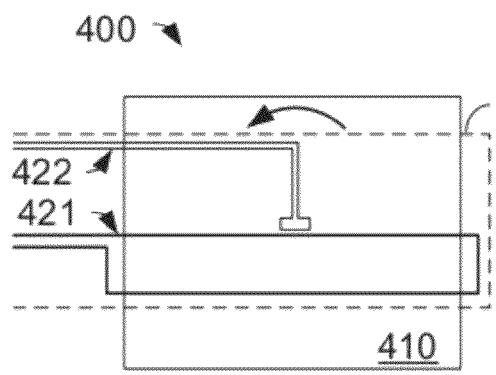
FIG. 4A-4D is a diagram showing rotation of a sensor on a composite material to determine fiber orientation, according to some embodiments.
Figure 4B:
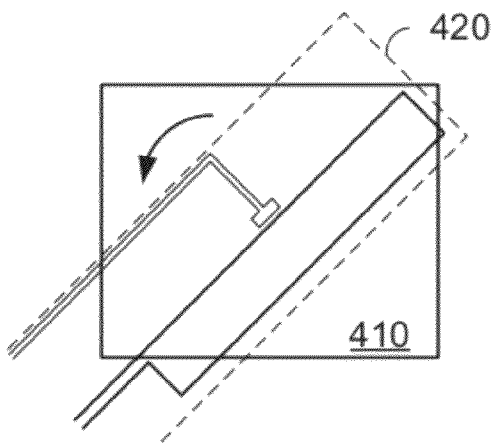
Figure 4C:
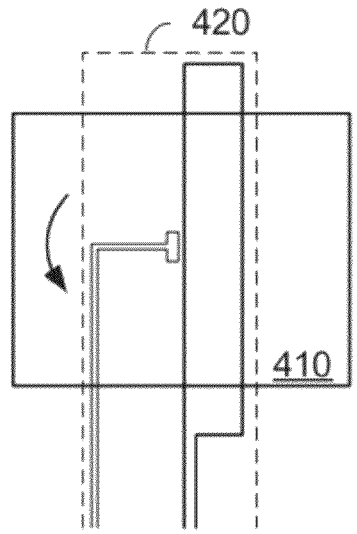
Figure 4D:
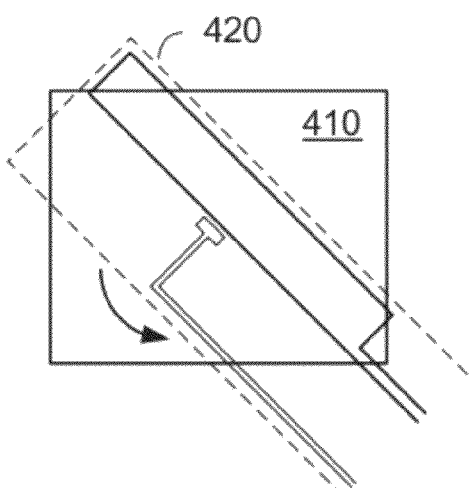

FIG. 4A shows conceptually a setup 400 for rotating a linear drive sensor 410 about a point on a test object 420 to determine fiber orientation as a function of angle. A mechanical fixture such as fixture 140 (FIG. 1) may be utilized maintain the linear drive sensor 410 proximal to the location on test object 420 to be inspected. The fixture facilitates rotation of the sensor relative to the location on the test object. Test object 420, sensor 410, or both may be actually rotated so long as the desired relative rotation is achieved.

A drive current is provided into drive winding 421 of sensor 410 and impedance responses are measured on sense element 422 as sensor 420 is rotated. Rotation may be performed by hand or may be facilitated by a suitable fixture. FIGS. 4A-4D show the sensor in various stages of rotation to further illustrate the measurement process. Impedance measurements may be made by suitable instrumentation (not shown) throughout the rotation process. For example, instrument 110 (FIG. 1) or another suitable instrument may be used. Note that while only one sense element is shown, sensor 420 may have multiple sense elements. The sense element closest to the axis of rotation may be selected for measurement and analysis. In some embodiments, another type of sensor may be used, for example, a meandering winding eddy-current sensor.

Figures 5A, 5B:
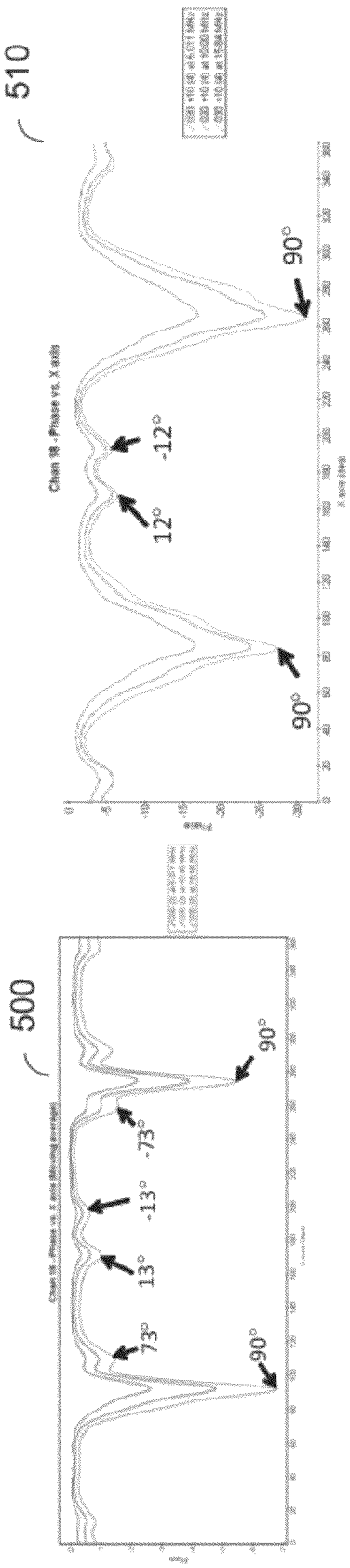
FIG. 5A shows measurement results obtained by rotating a sensor about a location on a composite material to determine fiber orientation.
FIG. 5B shows a table of the designed fiber wrap angles for the test specimen measured in connection with FIG. 5A.

An FA28 MWM-Array sensor from JENTEK Sensors, Inc. was used to verify the fiber layup on a composite overwrapped pressure vessel (COPV) and the phase of the impedance measurement results are shown as a function of measurement angle in plot 500 of FIG. 5A. The relevant dimensions of the FA28 sensor are shown in table 520 FIG. 2C. The COPV was inspected on the outside surface near the middle with respect to the axis of the bottle.

Impedance measurements were taken during rotation at multiple frequencies. In plot 500, the phase response at three frequencies, 5.011, 10.0 and 15.84 MHz, is shown. The largest impedance phase change occurs at the highest frequency shown, 15.84 MHz. The phase response has shifts that correspond to the fiber orientations. The valleys of the shifts indicate there are fibers in the hoop direction (90°) and helical fiber wraps at ±73° and at ±13°.

The composite overwrap ply layup specified by the manufacturer is listed in table 210 shown in FIG. 5B. Layer number 1 is the layer closest to the liner and layer number 5, which is a glass hoop wrap, is on the outer surface of the COPV. According to the manufacture, the carbon fiber overwrap consists of one layer of hoop fibers, a high angle fiber wrap at 72° and two low angle helical wraps at ±9.28°. The linear drive sensor measurements show all these orientations.

A relationship module may be used to identify the location of the fiber wraps of the test object. In some embodiments, local minima within the phase response may be used to identify the orientation of the fiber wraps. A threshold may also be used to reduce the probability that the minima are associated with noise or another signal source not indicative of fiber wrap orientation. This operation is merely illustrative and the relationship module may operate in any suitable way to identify fiber wraps directions. For example, the relationship module may identify fiber wrap locations from the sensor measurements as represented by the magnitude, phase, real or imaginary components, or after processing of the data to estimate material properties such as conductivity (e.g., using the above described Grid Methods). The relationship module may be implemented in software, hardware, or any suitable combination thereof. In some embodiments, the relationship module is one of modules 109 of instrument 110.

The fiber layup determined for the test object by the relationship module may be validated by a validation module. Like the relationship module, the validation module may be implemented as one of modules 109 of instrument 110. The validation model may be used to determine whether the layup of the test object is within a design specification.

It should be appreciated that selection of an appropriate sensor geometry and measurement signal (e.g., excitation frequency) is necessary to resolve each layer. The measurement was repeated with an FA24 sensor, also from JENTEK. The FA24 has the geometry of sensor 210 shown in FIG. 2B. The phase response measured with the FA24 is illustrated in plot 510 of FIG. 5A. This sensor response show fibers oriented in the hoop (±90°) direction, as well as helical fiber wraps at about ±12°, but does not show the high angle helical wrap observed with the FA28. Also the 90° peak is much broader for the FA24 and seems to mask masks the response from the ±73° helical wrap. Thus, while the FA24 is suitable for observing some of the fiber orientations, it was unable to resolve some of the fiber wraps at any of the plotted frequency.

Figure 6:
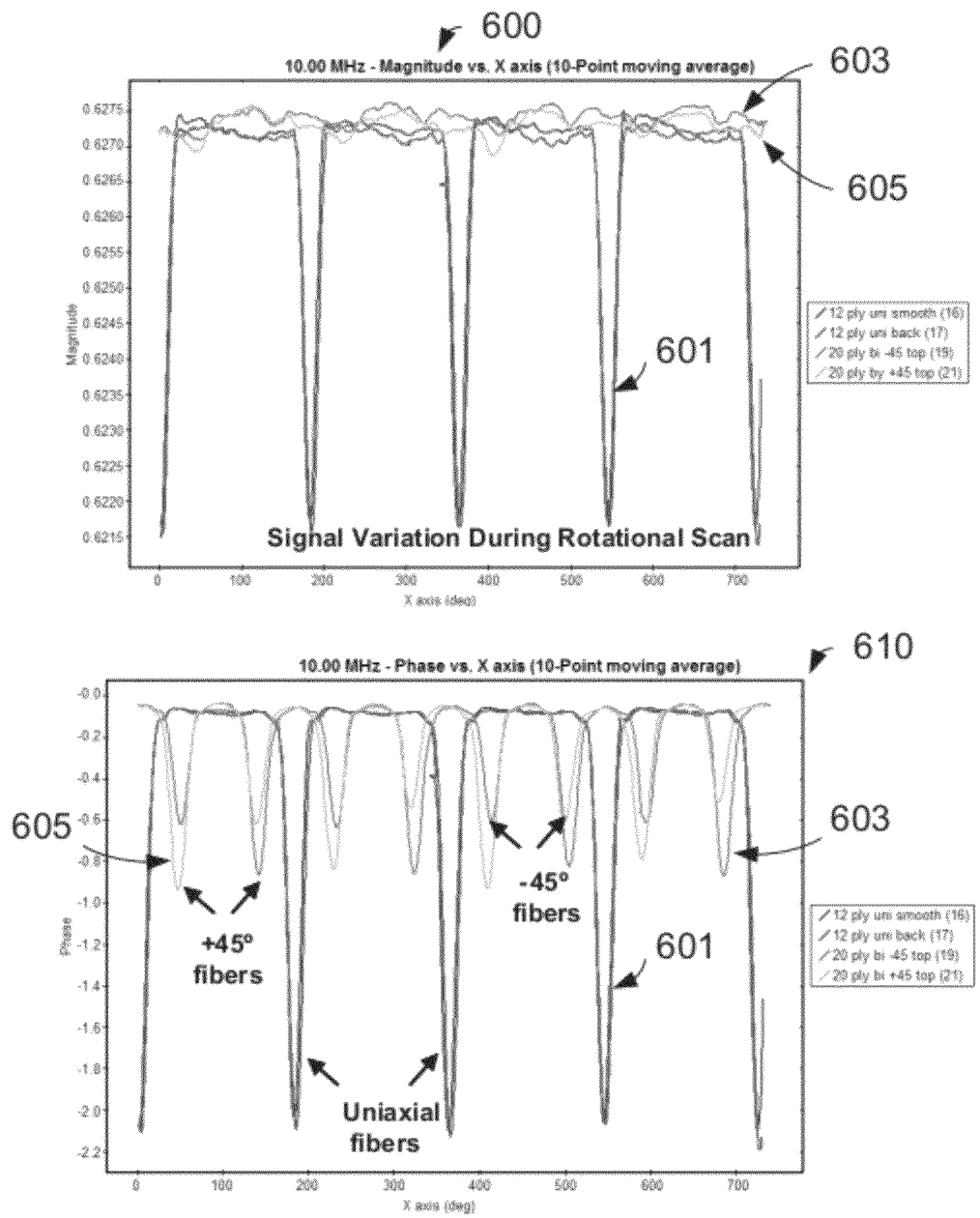
FIG. 6 shows magnitude and phase plots of a meandering winding eddy-current sensor response as a function of sensor orientation angle on several different carbon fiber composite samples.

FIG. 6 shows a magnitude plot 600 and phase plot 610 of an FS33 sensor response as a function of sensor orientation angle on several different carbon fiber composite samples. Line 601 is actually two lines representing nearly identical responses measured from opposite sides of a 12 ply uniaxial carbon fiber specimen. Notice the strong response every 90°. Lines 603 and 605 represents the response of a 20 ply specimen with carbon fiber plies at ±45°.

Figure 7:
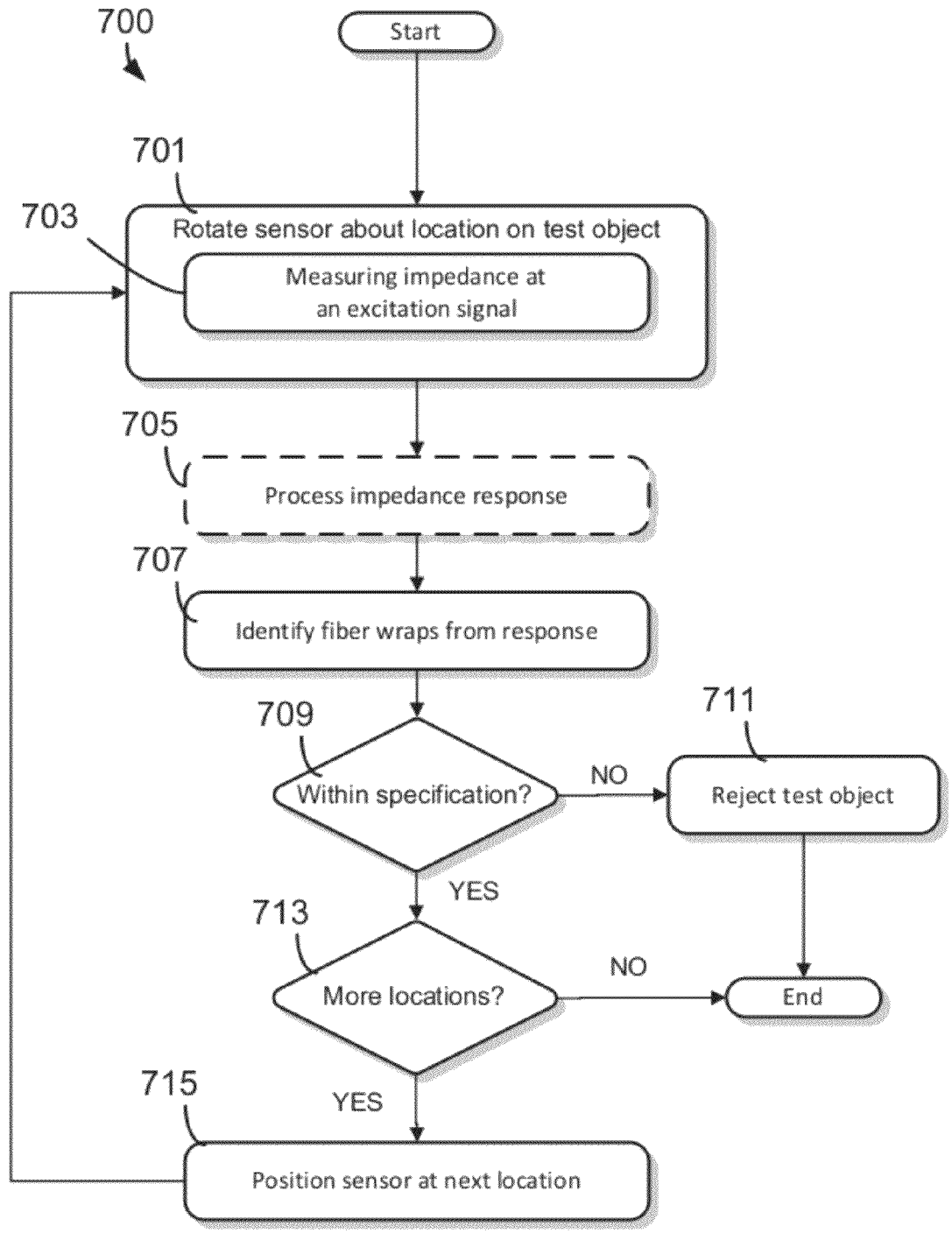
FIG. 7 is a method 700 for evaluating fiber orientation of a composite test object according to some embodiments.

FIG. 7 shows a method 700 for evaluating fiber orientation of a composite test object.

At step 701 the sensor is rotated about a location on the test object.

At step 704, which is performed during the rotation step 702, a sensor response to an excitation signal.

At step 705, the sensor response data is processed. For example, the sensor response may be related to sensor lift-off, effective conductivity, or any other suitable parameter. Though, it should be appreciated that raw sensor response data may be sufficient for determining fiber wrap directions.

At step 707, fiber wrap directions are identified from the data.

At step 709, a determination is made whether the fiber wraps at the location on the object are within specification.

If the fiber wraps are not within specification, method 700 may continue to step 711 at which the test object is rejected for failure to meet the specification.

If the test wrap is within specification a determination is made at step 713 whether there are more locations to scan. If not the method may end.

If there are more positions to inspect, method 700 may continue to step 715. At step 715 the sensor is positioned for scanning at the next location.

It should be appreciated that many variations of this method are possible and not all steps are required. For example, a determination may be made at each location if at the location the fiber wrap is within specification, but rejection of the test object may be based on other criteria, for example, a certain percentage of the inspected locations must fail for rejection.

In some embodiments the measurement may be repeated at multiple locations on the test object to obtain an understanding of the fiber layout at multiple locations on the test object. An automated or semi-automated fixture may be used to facilitate testing at the one or more locations.

In some circumstances the distance to each fiber layer may be estimated. Therefore the sensor may be used to interrogate the composite and determine, for example, the distance from each ply to the sensor. This distance may be used to estimate the termination of fiber layers as the distance from the sensor to the ply that drops off will abruptly increase to infinity, essentially, signaling that that ply is no longer part of the stack up. This may be achieved by scanning the sensor from a region where a given ply is extant to where it is not, for example, over a ply drop-off. Similarly, if the sensor is aligned with the ply and scanned "backwards" onto the drop off point, the arrival of the new ply may be detected.

Though much of the above discussion has focused on use of an eddy-current sensors, it should be appreciated that other sensor types, such as capacitive sensor used to interrogate low conductivity composites, may also be used.

The ability to identify the orientation of the fibers in a composite material may be used in configuring linear drive sensors for measurement of material properties. For example, a linear drive sensor may be aligned with a fiber direction in a material such that it is sensitive to specific layer(s) of a multi-directional fiber lay-up, where the response of the linear drive sensor is dominantly associated with the properties of the layer(s) having fibers oriented parallel to the linear drive. The linear drive sensor may have multiple linear drive segments. Using multiple segments of the linear drive, each potentially operating at multiple frequencies, the responses from multiple, distinct layers with fibers oriented parallel (or nearly parallel) to the linear drive, where the distinct layers may be all on one side of the sensor, but at different distances, or they may be both above and below the sensor, may be distinguished. The properties of the distinguished layers may be related to mechanical properties in a specific layer or layers. For example, the mechanical property may be stress or temperature.

In another embodiment the orientation of a linear drive sensor is aligned a few degrees off of parallel to the dominant fiber direction so that the sensor response (e.g., phase), exhibits a maximum or nearly maximum change of response with orientation angle so that a scan of the part would exhibit maximum or nearly maximum deviation of the sensor property with angle of the fiber layer/s below the sensor, to enable a sensitive measure of defects such as fiber wash or fiber waviness. These features may be identified algorithmically, using visual representations such as a scan image color map of the sensor property, or in any other suitable way. Constructing the sensor with sensing elements at various distances from the drive (segmenting the field) and operating the sensor across a band of frequencies may enable determination of both the angle(s) and depth(s) of fiber orientations inside the material.

In one aspect a function is used to represent a distribution or a property such as a fiber density distribution of an electrical conductivity distribution for a defined area or position on a material under test. In one such embodiment said distribution represents either a fiber property or a matrix property for a composite. In one such embodiment this function is desired for a baseline after production and the change in this function with aging or controlled thermal exposure or application of a load is measured to assess quality, condition, aging or damage. In one such embodiment the function is a probability distribution for fiber density or a volumetric conductivity at an impact damage site. In one such embodiment this function is used to monitor the evolution of fatigue damage at the impact damage site. In any of the above embodiments a linear drive ET sensor is used to capture an image that is in-turn used to derive said function for a composite. In one such embodiment the function is an estimation of fiber density and the changes are used to estimate strain. In another such embodiment the function represents the matrix of a relatively insulated composite and the function varies with applied frequency of the sensor drive input and the function is used to track thermally induced aging.

Another aspect relates to impact damage detection for a composite material.

In this section methods and apparatus are further detailed for detecting a characterizing damage to composite test objects such as COPVs. Detection and characterization of damage in liner materials such as those used in COPVs are also described. In some embodiments, a linear drive eddy-current sensor (e.g., MWM-Array) is used to scan a COPV. For example, the linear drive may be aligned in a fiber wrap direction to improve observability of damage. For example, the linear drive sensor may have the drive winding construct aligned in the hoop direction, the direction of a low angle helical wrap, or the direction of a high angle helical wrap. The linear drive eddy-current sensor may be excited at a relative high frequency (e.g., 1-15 MHz) as it is scanned across the COPV. Any suitable portion of the COPV surface may be scanned. For example, a surface of the COPV that will be exposed to impact damage may be scanned. The impedance measurements from the sensor may be converted into conductivity and lift-off measurements based on the sensor geometry and a model of the COPV. Lift-off represents the distance between the sensor and the conductive surface. This preliminary scan may serve to detect damage and/or act as a baseline for which to compare future scans. Damage can be detected, for example, as localized decreases in the conductivity.

At the same time, the sensor may be excited at a relatively low frequency (i.e., sub MHz, e.g., 50 kHz) to inspect the liner. This may be done by producing a dual frequency signal with both the high frequency signal and the low frequency signal, or may be produced by alternating excitation frequencies of the sensor. Again the impedance measurements may be converted to lift-off and conductivity, for example, using an appropriate model and the Grid Methods. Damage (e.g., dents) in the liner may be detected as localized increases in lift-off as at the lower frequency excitation, the composite overwrap may contribute primarily to lift-off and not substantially affect the conductivity measurements. In such a case the measured conductivity will be substantially that of the COPV liner.

In some embodiment a different sensor geometry may be used to interrogate the liner of the COPV. For example a circular or non-linear drive winding sensor may be used to excite eddy currents in the liner. Because of the non-linear drive winding geometry a higher frequency may be used. For example, the same frequency as used with the linear drive eddy current array to inspect the composite may be used. This may be performed during the same or separate scan of the COPV.

Previous scans of the COPV may be used as baseline scans to which a comparison can be made after later scans to determine if damage to the COPV has occurred in the interim between scans. The baseline scan image may be registered (i.e., spatially aligned) with the present scan image and subtracted there from to produce a change in property image. In the case of the composite, for example, a change in conductivity image may be produced. In the case of the liner, for example, a change in lift-off image may be produced. A damage detection threshold may be set to identify locations of possible damage. For example, a decrease in conductivity by a predetermined amount or more may be identified as a damage site in the composite. The amount of change in conductivity in the composite may be used to identify the severity of the damage to the composite. Similarly, the change in lift-off may be used to characterize damage in the liner. For example, the greater the increase in lift-off between the baseline image and the present image the larger the dent in the liner.

In some embodiments, the COPV may also include a multi-layer insulation (MLI). Depending on the thickness and conductivity of the MLI, the inspection may be done through (i.e., without removal) of the MLI.

While a scanning mode has been described above, a permanently mounted or embedded sensor configuration may be used in some embodiments.

Figure 8:
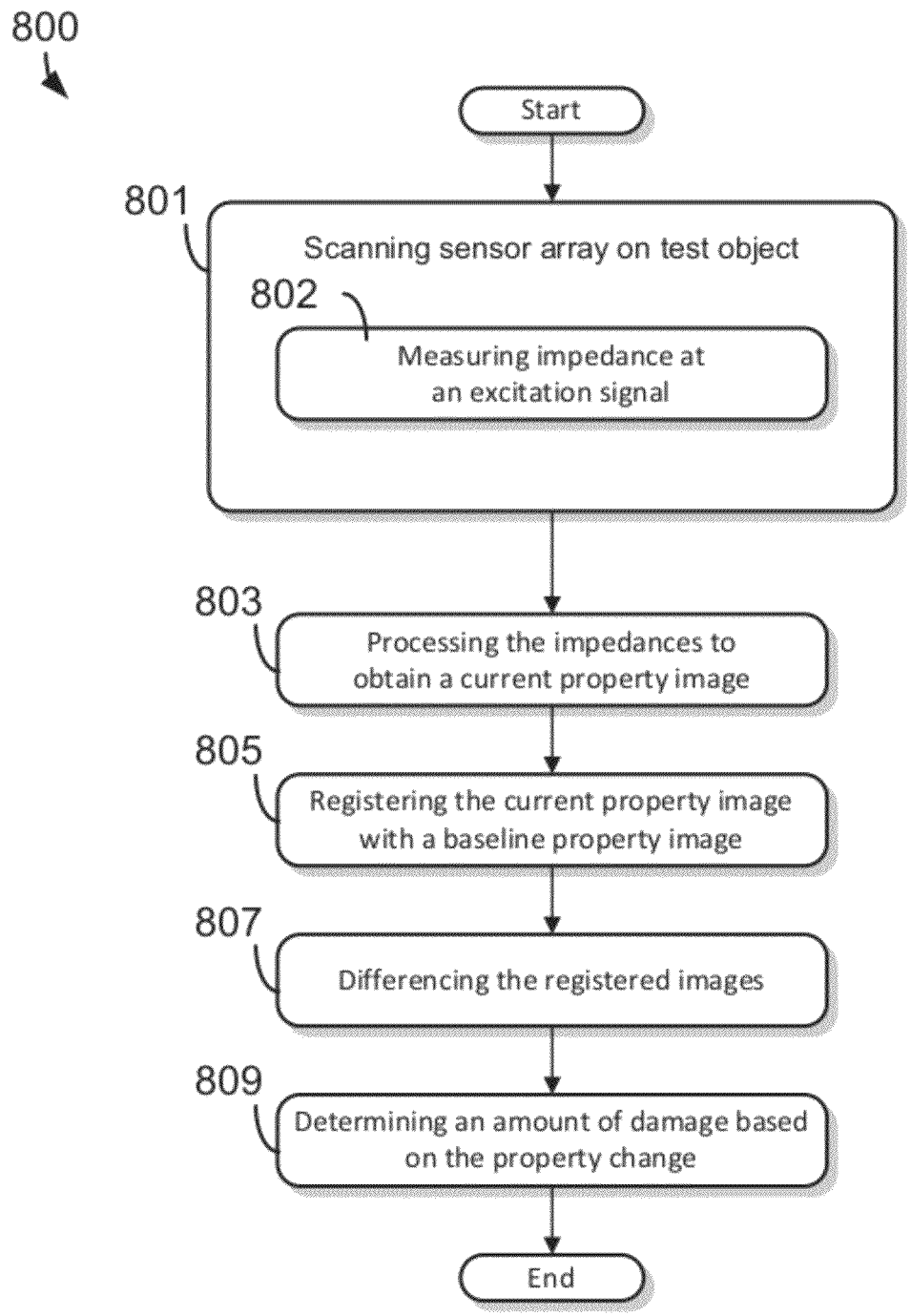
FIG. 8 is a method of inspecting a test object to identify damage according to some embodiments.

A method 800 of inspecting a test object is shown in FIG. 8. This method may be performed using system 100 (FIG. 1). Though, method 800 may be implemented in any suitable way. The test object may be a composite object, an object with composite and non-composite portions such as a COPV, or any other suitable type of object.

At step 801, a sensor is scanned across a surface of the test object. The sensor may be, for example, a linear drive eddy-current sensor array. The sensor and test object may be held by suitable a suitable fixture that ensures the sensor is held in compliance with the test object and may have motion control devices (e.g., motors) and position encoding devices to actuate and facilitate recording of the sensor position relative to the test object. The sensor may be suitably oriented with respect to the test object. For example, a drive conductor may be aligned with a fiber wrap orientation At step 802, which is performed during step 801, a series of measurements are taken and recorded. If an array is used, a series of sensor measurements may be recorded for each of the array elements. The sensor measurement results may be associated with the position of the sense element relative to the position of the test object at the time of measurement so that an image can later be formed for the scanned imaging area. Sensor measurements may be taken for one or more excitation signals. For example, sensor measurements may be recorded for each of multiple excitation signal frequencies. The sensor measurements may be recorded as impedance, admittance, or any other suitable representation of the response.

At step 803, the sensor responses are processed to obtain a property image of the test object in its current condition. The property image may represent an electromagnetic property, a geometric property, or any other suitable property of the material. In some embodiments, the sensor measurements are processed using Grid Methods to estimate the material property. Though, any suitable approach may be used. Step 803 may begin after each measurement is recorded (e.g., while scanning continues) or may be commenced after complete or partial scan results are available. When the measurement results are processed is not critical.

At step 805, a "baseline" property image is registered with the current property image generated at step 803. The baseline property image is a property image obtained from sensor data obtained from the test object at a previous time. For example, the data for the baseline property image may be obtained at a previous inspection of the test object, as part of manufacturing of the test object or at any other suitable time. Registration is a process whereby the images are lined-up with one another so that at each location of the current and baseline property images is registered with the same location on the test object. Those skilled in the art will recognize numerous techniques for registering images are known and any suitable approach may be used. For example, the images may be represented as two respective tables of equal dimension and each cell within the table may be registered by associating it with the corresponding cell of the other table. To illustrate another approach, where the location of the data values of the two images do not correspond sufficiently, one image may be interpolated to produce data values at the same locations represented in the other image. As yet another approach, the images may have registration marks therein which may be aligned by scaling, stretching and skewing one of the images. How the registration is performed is not critical.

At step 807, the registered images are differenced to identify the change in material property between the baseline scanning and the current operation. A difference image is generated as a result of the subtraction at this step.

At step 809, the difference image is analyzed to identify damage locations and the amount of damage sustained. Damaged areas may be identified by exceeding a threshold change in material properties. Where the damage mode of interest is impact damage, substantial and localized material property changes may be used to identify damage locations. In some embodiments, impact damage location detection is automated by a detection module. Detection module may be a module 109 of instrument 110. It should be appreciated that in some cases a background material property change may be present that is not associated with impact damage. Global material property changes in the test object may be associated with aging of the material.

Figure 9:
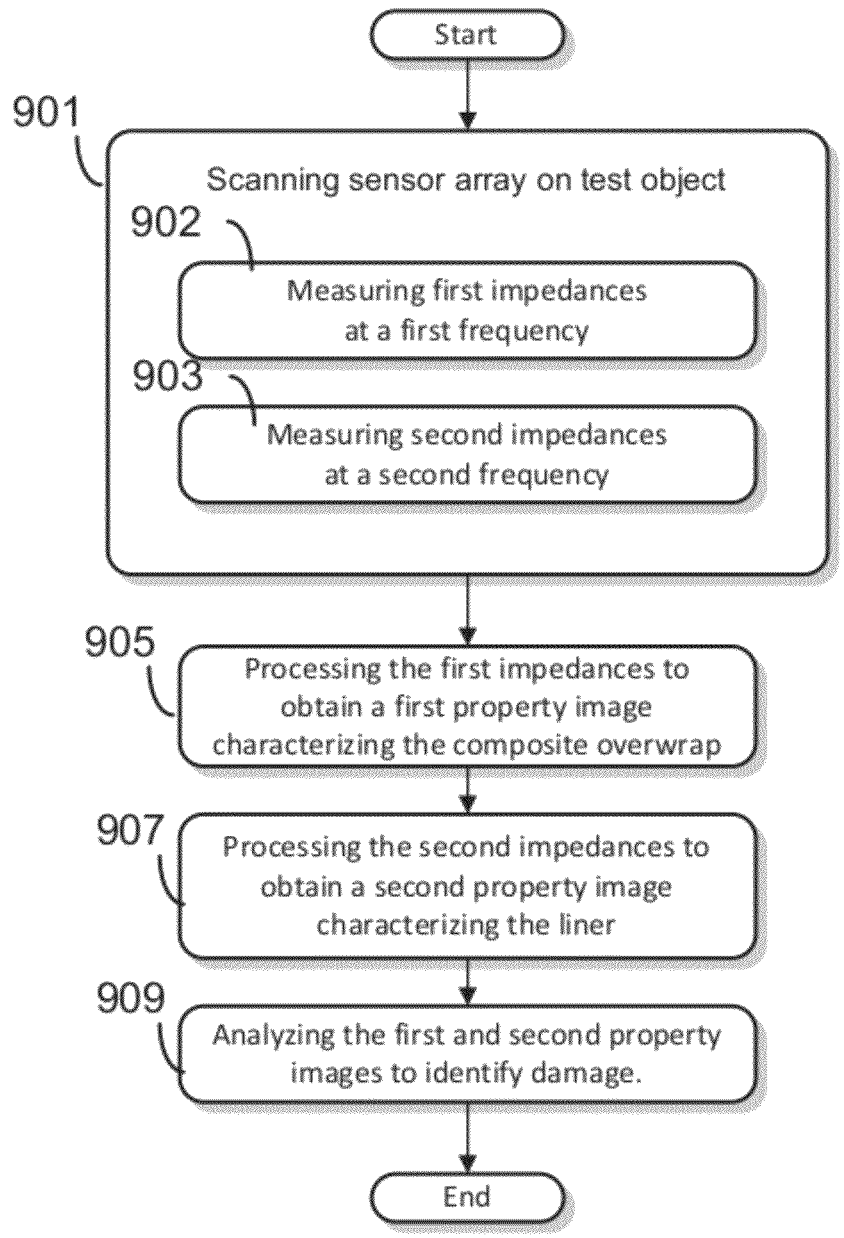
FIG. 9 is another method of inspecting a test object to identify damage according to some embodiments.

A method 900 of inspecting a composite overwrapped test object with a metal liner is shown in FIG. 9. This method may be performed using system 100 (FIG. 1). Though, method 900 may be implemented in any suitable way.

Method 900 is similar to method 800, however, method 900 includes additional steps of obtaining data at a second frequency.

At step 901, the sensor array is scanned on the test object. Step 901 may be performed in substantially the same way as steps 801 of method 800.

At step 902 impedances are measured at a first frequency for each of the sense elements of the array during the scanning at step 901. Step 902 may be performed in ways similar to those described in connection with step 802 of method 800. The first frequency may be chosen to obtain sensitivity to the composite overwrap portion of the composite.

Also during scanning, at step 903, impedances are measured at a second frequency for each of the sense elements of the array. The second frequency may be selected to penetrate through the composite overwrap for imaging of the metal liner. Steps 902 and 903 may be performed by switching the excitation of the drive winding back and forth between the first and second frequency or the first and second frequency may be superimposed and the responses separated using, for example, Fourier transform theory. Though, steps 902 and 903 may be performed in any suitable way.

At step 905, the impedance measurements at the first frequency obtained at step 902 are processed to image the composite overwrap. In some embodiments, the imaged feature of the composite overwrap is the effective conductivity of the overwrap which is estimated using a conductivity/lift-off grid and the Grid Methods. Though, the impedance measurements may be processed using any suitable inverse method to estimate a property of the composite overwrap which may be used to indicate damage to the overwrap.

Similarly, at step 907 the impedance measurements at the second frequency obtained at step 902 are processed to image the metal liner. In some embodiments, the imaged feature of the metal liner is the effective distance between the sensor and the liner. This may be estimated using a conductivity/lift-off grid and the Grid Methods. Note that if a conductivity/lift-off grid is used, the composite overwrap is assumed to be of much lower conductivity than the metal liner such that the sensor is substantially unaffected by the conductivity of the overwrap. It should be appreciated, however, that the impedance measurements may be processed using any suitable inverse method to estimate a property of the metal liner which may be used to indicate damage to the liner.

At step 909, the property images formed at steps 905 and 907 are analyzed to detect damage to the composite overwrap and the metal liner respectively. In some embodiments, damage to the composite overwrap is identified by local regions of low conductivity and damage to the metal liner is identified by localized regions of high lift-off. In some applications it may be anticipated that damage to the liner will also be associated with damage to the overwrap at the same location on the test object. Registration with and subtraction of baseline images of the test object as described generally in connection with steps 805 and 807 of method 800 may also be used as part of the analysis of the property images to detect damage.

It should be appreciated that method 900 may be implemented using different sensors rather than different excitation frequencies to differentiate the liner and the composite overwrap. For example, a sensor having a drive winding that is not aligned with a fiber wrap within the composite overwrap or with a non-linear shape may be used.

To demonstrate the methods a COPV vessel was scanned in accordance with methods 800 and 900. The COPV vessel has an aluminum liner and a composite overwrap made up of primarily carbon fiber composite materials. Data was taken before impact damage to be used as a baseline result. The COPV was scanned axially on the constant radius cylindrical section of the bottle with both FA24 and FA28 sensors from JENTEK (see FIGS. 2B and 2C, respectively). Because these sensors are not wide enough to inspect the entire circumference in a single pass, a fixture was developed to scan along the axis, return the sensor to the starting position, rotate the COPV so that there was a slight overlap between scans and repeat until the entire circumference was covered. The methods were repeated at two sensor orientations: the hoop (90°) orientation and an orientation parallel to the major helical wrap orientation of about 10°. The sensor for the major helical wrap orientation was set by rotating the sensor until a local peak in the signal was achieved. (See the discussion above regarding fiber wrap detection.)

Figure 10A:
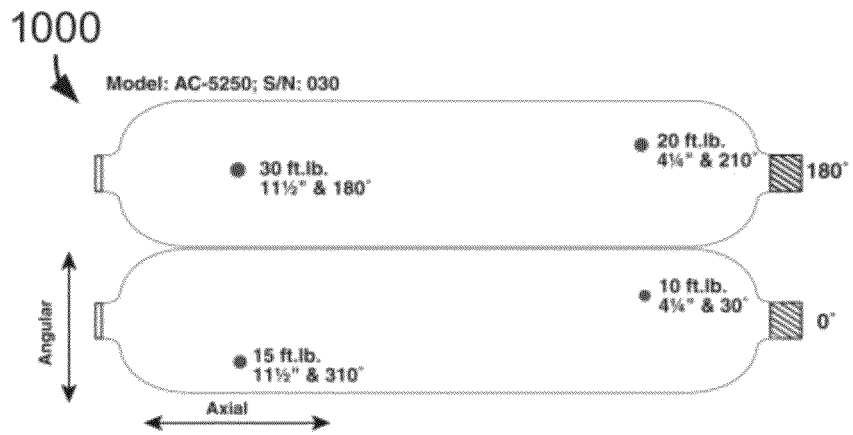
FIG. 10A is a schematic showing impact locations on a COPV specimen.

After the baseline scans were completed, the COPV was subject to controlled impact damage at four locations. The impact energies used were 30 ft-lbs, 20 ft-lbs, 15 ft-lbs and 10 ft-lbs. The locations of the impact sites and the respective impact energies are show in schematic 1000 of FIG. 10A.

In the imaging results, the baseline and after impact damage results are shown. The baseline subtracted image, which is also presented, is obtained by subtracting the baseline C-scan from the C-scan image after impact damage.

Two approaches were used to perform registration and subtraction of the baseline image. In the first approach a common feature is found and the images are shifted to have common x-y coordinates and then the baseline C-scan image is subtracted from the C-scan image after impact damage. This method is most effective if the sensor orientation before and after impact are nearly identical since the sensors response is sensitive to the drive orientation relative to the fiber axis. In the second approach small differences in sensor orientation could be compensated by a small image rotation before the subtraction. This method requires the images to be normalized so when the subtracted image is presented the property images shows relative rather than absolute conductivity change.

Figure 10B:
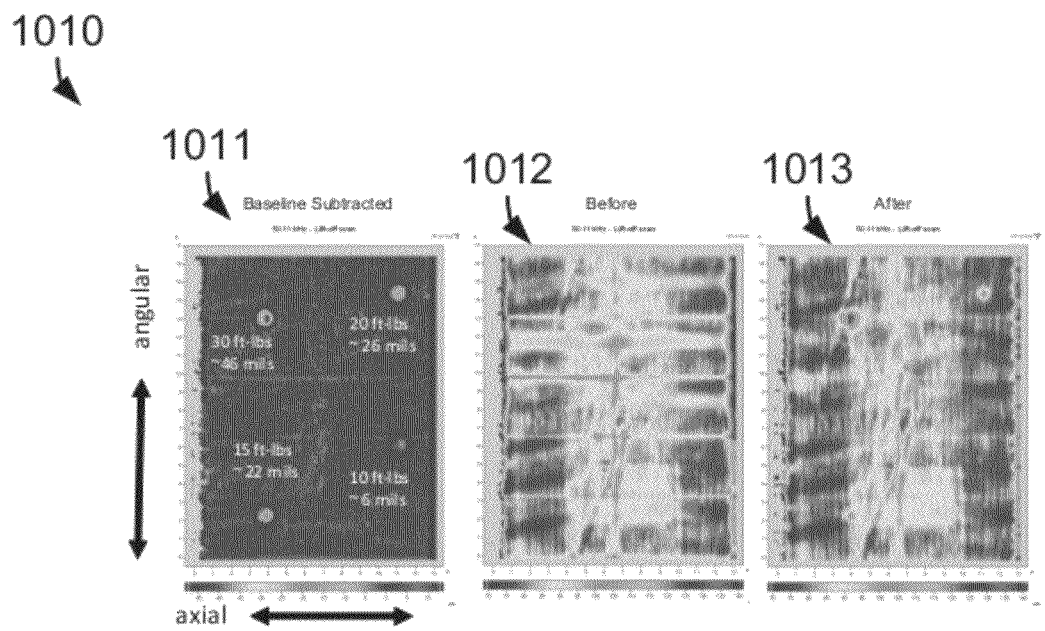
FIG. 10B shows before, after, and baseline subtracted images of sensor lift-off to image liner damage on a COPV at 50 kHz.

Images 1010 in FIG. 10B show a lift-off C-scans at 50 kHz with the FA24 MWM-Array. Specifically images 1010 include a before impact damage image 1012, an after impact damage image 1013, and a baseline subtracted image 1011. At 50 kHz, the properties of the aluminum liner are being measured. Image 1011 clearly shows the four impact sites and an estimation of the lift-off change indicates the amount that the impacts have dented the aluminum liner. At the highest impact energy, 30 ft-lbs, the dent is estimated to be 46 mils in depth and at the lowest impact energy, 10 ft-lbs, the dent is estimated to be 6 mils in depth.

Figure 10C:
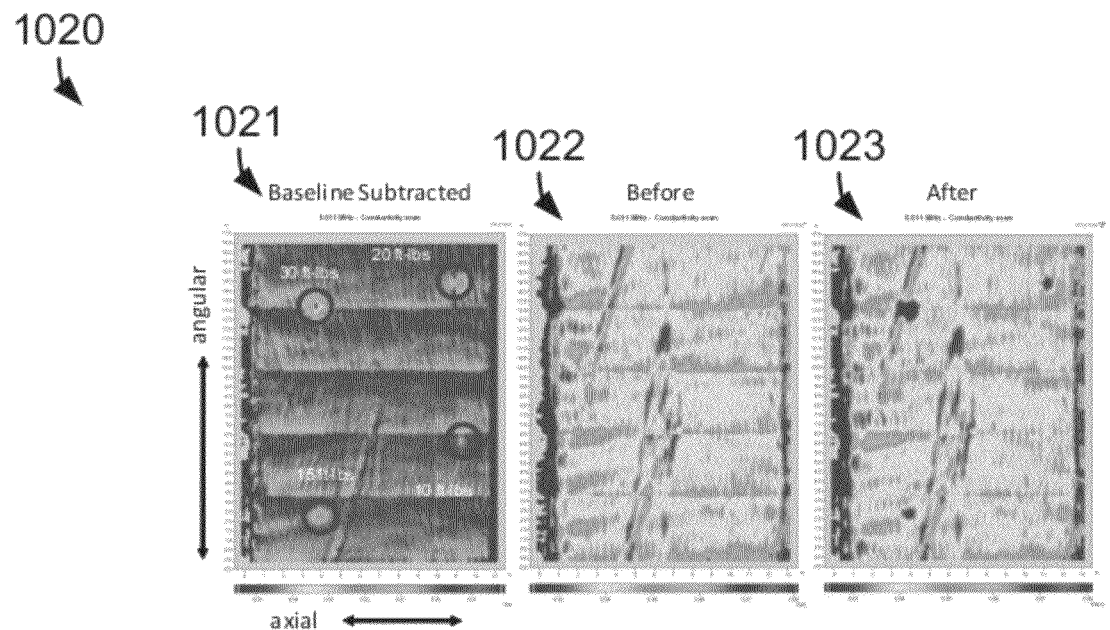
FIG. 10C shows before, after, and baseline subtracted images of conductivity to image damage to the composite overwrap of a COPV at 5 MHz.

Images 1020 in FIG. 10C shows the conductivity C-scan at 5.011 MHz for the FA24 MWM-Array. Images 1020 include a before impact damage image 1022, an after impact damage image 1023, and a baseline subtracted image 1021. Image 1021 clearly shows a conductivity decrease at each of the four impact sites, with the site with the highest impact energy showing the largest conductivity change and the largest area of decreased conductivity.

Figure 10D:
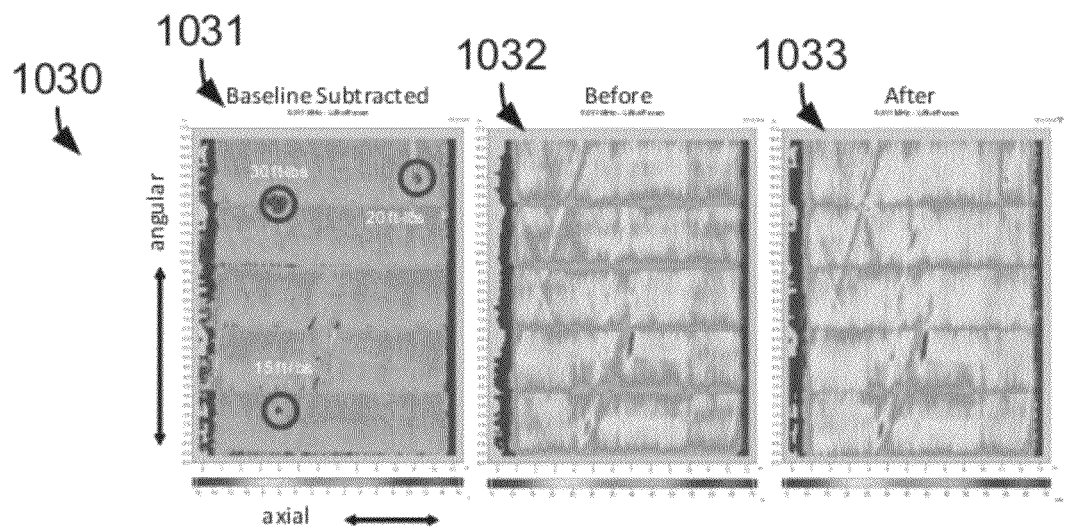
FIG. 10D shows before, after, and baseline subtracted images of sensor lift-off to image liner damage on a COPV at 5 MHz.

Images 1030 in FIG. 10D shows the corresponding lift-off C-scan at 5.011 MHz. Images 1030 include a before impact damage image 1032, an after impact damage image 1033, and a baseline subtracted image 1031. The impact damage site with the largest impact energy shows the largest lift-off change and the damage are with the smallest impact energy shows no change, however the conductivity image at this location does show some conductivity decrease. Conductivity C-scan at frequencies of 3.162 MHz, 10 MHz and 15.84 MHz, which were used to image the composite overwrap, showed similar results to those presented at 5.011 MHz. The conductivity C-scans with the FA28 showed results similar to the FA24 results.

Figure 11:
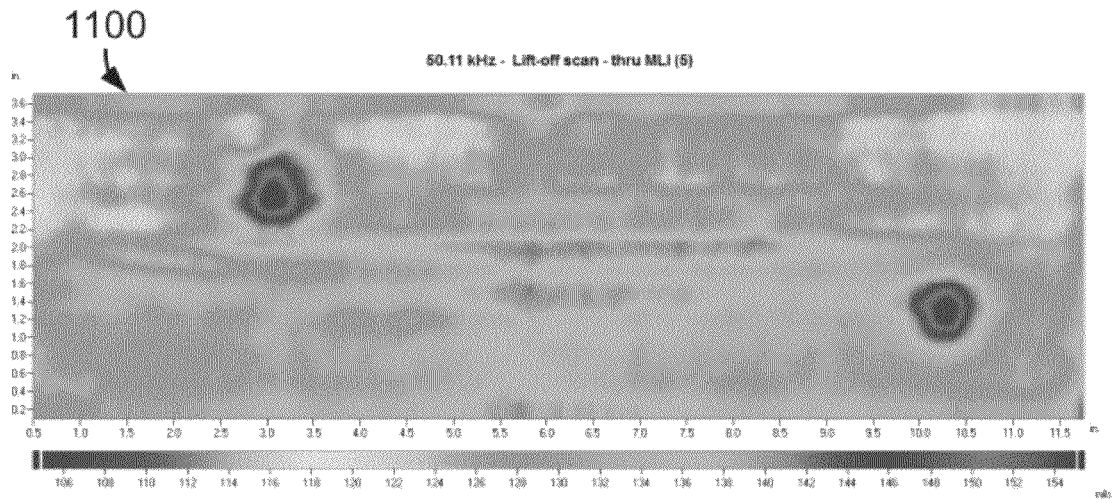
FIG. 11 shows an imaging of COPV liner damage through multi-layer insulation (MLI)

A multi-layer insulation (MLI) may be used to cover some COPVs. Inspection through such a layer is often desirable. Such MLI may be up to ¼ an inch in thick, for example. Methods 800 was demonstrated on a COPV through a relatively thin (0.0375 inches) MLI layer. The impedance measurements were processed using three unknown grids and the grid methods. The three unknown parameters were conductivity, lift-off and thickness to obtain an accurate conductivity value for the MLI. The MLI measured conductivity was 0.145% IACS, which is almost an order of magnitude higher than the conductivity of the carbon fiber overwrap (~0.025% IACS). However, the aluminum liner has a conductivity of 45% IACS. Detection of damage to the liner through the MLI insulation layer was demonstrated. Image 1100 in FIG. 11 shows the lift-off C-scan at 50 kHz with the MLI in place. The impact damage to the liner is clearly visible, with the damages areas showing an increase in the lift-off. The lift-offs for the MLI covered COPV are higher due to the added lift-off provided by the MLI. In another embodiment damage in an internal structural member such as a crack or corrosion is imaged through a composite. In one such embodiment the linear drive sensor is intentionally, not aligned with a fiber direction to ensure more applied field reaches the internal structural member. In an embodiment the damage is a crack in an internal metal spar in an aircraft wing structure.

Another aspect relates to volumetric stress measurements of a composite material.

Linear drive eddy-current sensors may be used to make volumetric stress measurements of composite materials. Stress measurements at different positions may be made using mounted arrays. Stress measurements at different depths may be made by using multiple excitation frequencies and/or multiple sensor geometries. That is, the characteristic sensor lengths associated with a sensor may be changed to achieve different depths of sensitivity within the test object. Different excitation frequencies may be controlled directly from the instrumentation driving the drive winding of the sensor. Different sensor geometries may be achieved by forming sensing elements at different distances from a common drive winding, physically separating the drive winding and sense elements (e.g., using separate substrates), or in any suitable way.

In some embodiments, a linear drive sensor is permanently mounted on a composite with linear fibers with the linear drive parallel or nearly parallel to the fibers such that a load applied to the composite displaces the fibers relative to the linear drive. This load-induced displacement may be in the direction of the fibers & linear drive, or it may be perpendicular to the direction of the fibers & linear drive. By monitoring the linear drive sensor across a band of frequencies, the load may be a function of depth beneath the sensor and inverse methods may be used to determine the load-vs-depth profile from the multi-frequency measurements.

In some embodiments, a linear drive sensor is permanently mounted on a composite with linear fibers such that a load applied to the composite displaces the fibers relative to the linear drive. The sensor is measured at two different loads to monitor changes in the load. The linear drive may have a periodic structure matching a periodic characteristic such as a repeatable fiber tow weave width where the spatially periodic sensor response is sensitive to changes in residual and applied stresses within the composite.

In another embodiment, a linear drive sensor is aligned such that it is sensitive to selected layers of a multi-directional fiber lay-up where the response of the linear drive sensor is dominantly associated with the properties of the selected layer. The property of interest of the selected layer may be stress, temperature, or any other suitable property.

In yet another embodiment a sensor is scanned across the part to baseline the fiber locations with a selected linear drive orientation. In one such embodiment mathematical statistics and/or a function is computed to define the fiber positions. The function may be, for example, a fiber density distribution as a function of position along the surface, response versus the partial domain frequency such as in a typical power spectrum density plot vs. spatial frequency. A second scan may be taken in the same orientation and changes from the baseline used to estimate a parameter such as strain or stress. The strain or stress may be estimated as a function of depth by changing lift-off, sensor geometry, frequency on another sensor operating condition. Multiple drive conductor orientations may be used to estimate stress or strain in different fiber orientations. The stress may be imaged over side areas with and without applied loads to assess structural condition and/or integrity.

In some embodiments, a linear drive eddy-current sensor is used to examine the condition of a layer with a predetermined fiber orientation. The linear drive sensor may be scanned across the part surface with the drive at an angle such that a linear drive conductor is aligned with the fiber orientation of interest. In one such embodiment a baseline is taken after a production stage or after production to qualify the condition for acceptance testing. In one such embodiment the baseline is stored for later use. Later inspections performed at the same surface are then combined (e.g., subtracted or otherwise mathematically combined) with the baseline to look for changes that represent aging or damage or stress in the composite. In one such embodiment scans (baseline and after service) are taken in multiple orientations, spatially registered and stored.

Another aspect relates to evaluating fiber tow density in a composite material.

System 100 of FIG. 1 may be used with a linear drive sensor to determine fiber tow density within a fiber ply. For example, a ply may have a weave with a repeated fiber tow weave width. The sensor may be scanned across the composite in the direction of the periodicity of the weave. That is the linear drive construct may be aligned with the fiber tows and the direction of scanning is perpendicular to the linear drive construct. The sensor response may vary so as to detect each tow in the weave. The spatial variation in the response may be inspected to identify aberrations in the weave. In some embodiments, the response is processed using a computing device to determine the spatial frequency of the sensor variation. For example, the spatial sensor response may be converted to the spatial frequency domain using Fourier theory or another suitable technique. The weave tow spatial frequency will produce a peak response in the power spectrum of the spatial frequency domain.

Figure 12A:
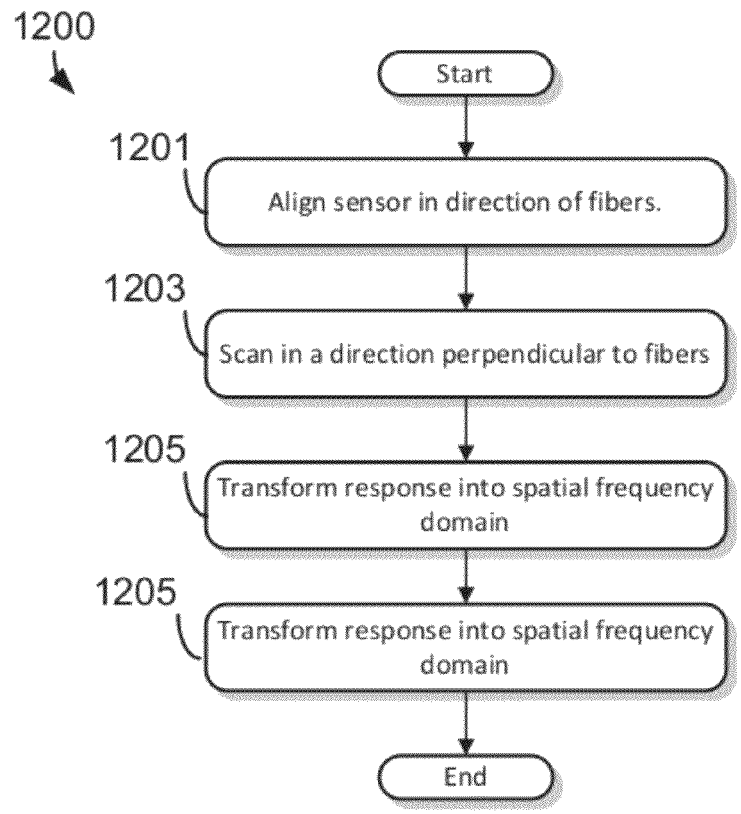
FIG. 12A shows a method for determining a periodic characteristic of a composite, such as repeatable fiber tow weave width, using a linear drive eddy-current sensor according to some embodiments.

A method 1200 is described in connection with FIG. 12A for determining a periodic characteristic of a composite, such as repeatable fiber tow weave width, using a linear drive eddy-current sensor. Method 1200 may be performed in any suitable way, for example, using system 100 shown in FIG. 1.

At step 1201, a linear drive eddy-current sensor is aligned with the direction of the fibers in the fiber tows.

At step 1203, the sensor is scanned in a direction perpendicular to the direction of the fibers, that is, in the direction of the periodicity of the fiber tows. During scanning impedance measurements are made from the sensor for one or more excitation signals. Scanning may be facilitated by one or more motors and scan position may be recorded using in any suitable way.

At step 1205, the sensor response is transformed into a spatial frequency domain response. The transition from the sensor response into the spatial frequency domain may be performed using approaches known from Fourier transform theory such as the fast Fourier transform (FFT) or any other suitable approach. Of course, equivalent transformations may be performed such as transformation into the spatial periodicity domain.

At step 1207, the fiber tow density is validated. In some embodiments, the spatial frequency domain information determined at step 1205 is used to determine the periodicity of the fiber tows, for example, by identifying a peak within the spatial frequency response, determining the corresponding spatial periodicity and comparing it with an acceptable range of spatial periodicities. The location of the spike-like feature appearing near the inverse of the spatial periodicity (modulo factors of 2 and pi, depending, for example, on Fourier conventions) may be determined via the mean, median, mode, or any one or more of various pulse-location metrics. An accept/reject determination may be made based on whether the estimated fiber tow density is within the specification.

In some embodiments, measurement at this location are performed at various loads to monitor changes in the load.

Figure 12B:
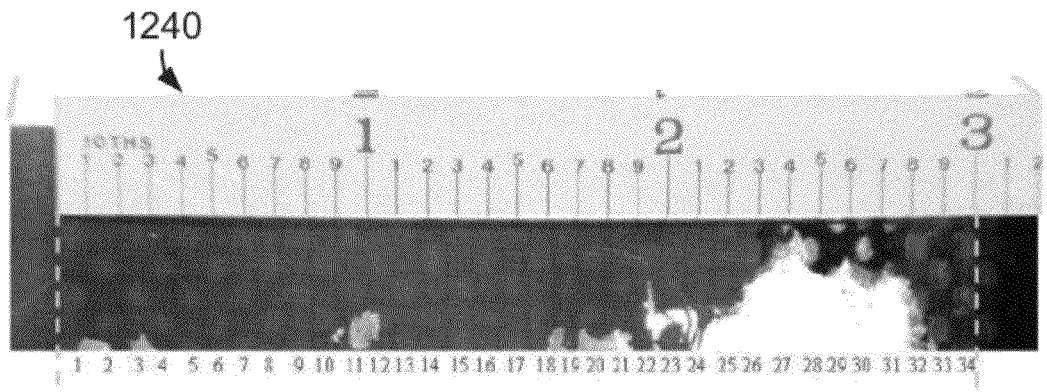
FIG. 12 B shows a composite specimen having regularly spaced fiber tows.
FIG. 12C shows the composite specimen having regularly spaced fiber tows with a sensor response superimposed thereon.
FIG. 12D show the power spectral density of the sensor response obtained by scanning in a direction perpendicular to the fiber direction.
Figure 12C:
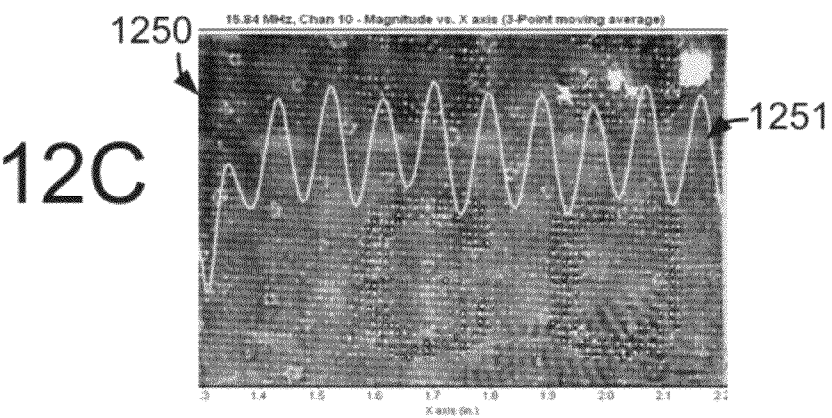
Figure 12D:
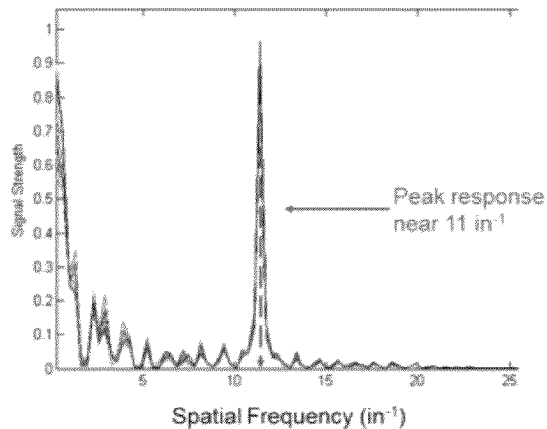

FIG. 12B shows an image 1240 of a composite sample with regular fiber tow spacing. FIG. 12C shows an image 1250 of the sample but with a magnitude 1251 of a sensor response superimposed thereon. Note that the sensor response is spatially periodic. The spatial frequency of the sensor response is represented in power spectrum density plot 1260 of FIG. 12D. The peak in response corresponds with the periodicity of the fiber tows.

The spatial periodicity may also advantageously be used to monitor changes in material properties such as residual and applied stresses within a composite. A linear drive sensor formed of two or more linear drive segments having a spatially periodic structure matching a periodic characteristic of the composite, such as a repeatable fiber tow weave width, may be mounted on the composite. With the drive segments aligned in the direction of the fiber of the fiber tows or another corresponding feature the sensor may be sensitive to material conditions such as stress.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A system for detecting impact damage to an object, the system comprising:
    an eddy-current sensor array having a plurality of array elements;
    a fixture for scanning the eddy-current sensor array over a surface of the object;
    an instrument for measuring impedances from each of the array elements of the array during scanning;
    a processor; and
    a plurality of modules comprising code executable by the processor, the plurality of modules comprising
    an imaging module to generate a current material property image from the impedances measured by the instrument; and
    a detection module to determine from the current material property image locations of impact damage.

2. The system of claim 1 further comprising a computer-readable storage device for recording a prior material property image obtained from impedance measurements of an earlier scan of the object, wherein the detection module subtracts the current material property image from the prior material property image to identify locations with material property changes in excess of a threshold.

3. The system of claim 1 wherein the material property is a local distance of the eddy-current sensor array to a surface of the object.

4. A method of inspecting a composite overwrap pressure vessel (COPV), the method comprising:
    scanning a linear drive eddy-current sensor array proximal to the COPV parallel to a surface of the COPV;
    measuring, during the scanning, first impedances at each of a plurality of sense elements of the array, while exciting the sensor at a first frequency;
    measuring, during the scanning, second impedances at each of the plurality of sense elements of the array, while exciting the sensor at a second frequency, lower than the first frequency;
    processing the first impedances to obtain a first property image characterizing the composite overwrap of the COPV;
    processing the second impedances to obtain a second property image characterizing a metal liner of the COPV;
    analyzing the first and second property images to determine damage in the composite overwrap and the metal liner of the COPV, respectively.

5. The method of claim 4, wherein the analyzing comprises:
    registering a previously captured image of the respective property and determining a difference between the two;
    comparing the differences to a respective threshold to identify locations of damage; and
    determining an amount of damage at the locations of damage based on an amount of change in the property.

6. A method of inspecting a composite overwrap pressure vessel (COPV) comprising:
    scanning an eddy-current sensor proximal to the COPV parallel to a surface of the COPV;
    during the scanning, measuring first impedances while exciting a linear drive of the sensor;
    during the scanning, measuring second impedances while exciting a non-linear shaped drive of the sensor;
    processing the first impedances to obtain a first property image characterizing the composite overwrap of the COPY;
    processing the second impedances to obtain a second property image characterizing a metal liner of the COPY; and
    analyzing the first and second property images to determine damage in the composite overwrap and the metal liner of the COPY, respectively.

7. A system for identifying defects in a low-conductivity fiber composite, the system comprising:
    a capacitive sensor;
    a fixture for scanning the capacitive sensor array over a surface of the low-conductivity fiber composite;
    an instrument for measuring impedances from the capacitive sensor during the scanning; a processor; and
    a plurality of modules comprising code executable by the processor, the plurality of modules comprising
    an imaging module to generate a current material property image from the impedances measured by the instrument; and
    a detection module to determine from the current material property image locations of defects in a low-conductivity fiber composite.

8. The system of claim 7, wherein the capacitive sensor is a capacitive sensor array.

* * * * *

UNITED STATES PATENT AND TRADEMARK OFFICE
CERTIFICATE OF CORRECTION

PATENT NO. : 8,928,316 B2  
APPLICATION NO. : 13/297933  
DATED : January 6, 2015  
INVENTOR(S) : Goldfine et al.

Page 1 of 1

It is certified that error appears in the above-identified patent and that said Letters Patent is hereby corrected as shown below:

In the Claims  
Column 22, Claim 6, Line 40 delete "COPY" and insert --COPV--  
Column 22, Claim 6, Line 42 delete "COPY" and insert --COPV--  
Column 22, Claim 6, Line 45 delete "COPY" and insert --COPV--

Signed and Sealed this  
Twenty-eighth Day of April, 2015

Michelle K. Lee  
*Director of the United States Patent and Trademark Office*